United States Patent
McGovern et al.

(10) Patent No.: US 7,959,639 B1
(45) Date of Patent: Jun. 14, 2011

(54) TRIALING SYSTEM AND METHOD UTILIZING OFFSET

(75) Inventors: Michael A. McGovern, Wyckoff, NJ (US); Michael Florentino, Ocean Grove, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 981 days.

(21) Appl. No.: 11/507,370

(22) Filed: Aug. 21, 2006

(51) Int. Cl.
  *A61F 2/00* (2006.01)
(52) U.S. Cl. ...................................... 606/102; 623/20.14
(58) Field of Classification Search ................... 606/88, 606/90, 102; 623/13.12, 20.14–20.36
  See application file for complete search history.

(56) References Cited

U.S. PATENT DOCUMENTS

| | | | |
|---|---|---|---|
| 2,691,899 A * | 10/1954 | Brown | 74/471 R |
| 5,290,313 A | 3/1994 | Heldreth | |
| 5,776,200 A * | 7/1998 | Johnson et al. | 623/20.15 |
| 5,782,920 A * | 7/1998 | Colleran | 623/20.34 |
| 6,063,091 A | 5/2000 | Lombardo et al. | |
| 6,149,687 A | 11/2000 | Gray, Jr. et al. | |
| 6,228,091 B1 | 5/2001 | Lombardo et al. | |
| 6,258,095 B1 | 7/2001 | Lombardo et al. | |
| 6,620,168 B1 | 9/2003 | Lombardo et al. | |
| 6,629,978 B2 | 10/2003 | Schulzki et al. | |
| 6,673,114 B2 * | 1/2004 | Hartdegen et al. | 623/19.12 |
| 6,740,092 B2 | 5/2004 | Lombardo et al. | |
| 6,953,479 B2 * | 10/2005 | Carson et al. | 623/20.15 |
| 6,974,481 B1 * | 12/2005 | Carson | 623/20.14 |
| 7,025,788 B2 * | 4/2006 | Metzger et al. | 623/20.15 |
| 7,044,975 B2 * | 5/2006 | Cheal et al. | 623/22.42 |
| 2001/0053935 A1 * | 12/2001 | Hartdegen et al. | 623/19.12 |
| 2003/0014120 A1 * | 1/2003 | Carson et al. | 623/20.21 |

* cited by examiner

*Primary Examiner* — Eduardo C Robert
*Assistant Examiner* — Christian Sevilla
(74) *Attorney, Agent, or Firm* — Arthur Jacob

(57) ABSTRACT

An improvement in a trialing system and method for use in connection with the implant of a prosthetic joint component having a first part for engaging bone at an implant site to secure the component at the implant site, and a second part for enabling articulation of the prosthetic joint. A trial first member corresponds to the first part of the component, a trial second member corresponds to the second part of the component, and an offset adapter facilitates selective coupling and uncoupling of the trial first member and the trial second member with the trial second member offset from the trial first member and placed at a selected angular orientation relative to the offset adapter. Thus, during a trialing procedure the trial second member is selectively released readily for replacement of the trial second member with alternate trial second members, and replacement of the offset adapter with alternate offset adapters, as well as facilitating the selected angular orientation of a trial second member relative to an offset adapter, as required in order to expedite an accurate trialing procedure.

19 Claims, 7 Drawing Sheets

TRIALING SYSTEM AND METHOD UTILIZING OFFSET

The present invention relates generally to trialing used in connection with the implant of prosthetic joint components and pertains, more specifically, to a trialing system and method in which an offset coupling arrangement enables quick and effective verification of the accuracy of the preparation of an implant site for the proper reception of a prosthetic joint component having an articulation part offset from a securement part of the prosthetic joint component.

Prosthetic joint components usually include a securement part, such as a stem for extending into bone at an implant site, and an articulation part, such as a bearing member which is attached to the stem. For example, in a knee prosthesis, a tibial component usually includes a stem for securement within the tibia, and a tibial baseplate, which is attached to the stem for receiving a tibial bearing member. A femoral component usually includes a stem for affixation within the femur, and a condylar member carried by the stem for articulation on the tibial bearing member.

During an implant procedure, a trialing system is employed to assure that the implant site is prepared accurately for the proper reception of the prosthetic joint components. Such trialing systems and methods utilize trial components placed temporarily at the implant site so as to simulate the intended positioning of the actual prosthetic joint components and thereby verify the accuracy of the implant site preparation, prior to permanently implanting the actual prosthetic joint components themselves. Because of variations in joint size and shape among recipients of prosthetic joints, the proper fitting of a prosthetic joint often requires that the articulation part and the stem part of a prosthetic joint component be offset relative one another. Thus, trialing systems and methods which incorporate offset arrangements have been developed to verify accuracy in the preparation of an implant site where offset is required.

Trial components typically are used in joint arthroplasty to verify that bone preparation at an implant site will receive the desired implant assembly, that the size and orientation are accurate, and that the joint mechanics have been recreated and are stable. When a surgeon determines that an offset is necessary to best match a particular patient's anatomy, a trial which incorporates offset is needed to complete an evaluation of the implant site preparation before the actual implant components are permanently implanted in the recipient.

Current trialing systems and procedures generally are based upon assembling trial component parts in a manner similar to the construction of actual implant components in order to establish a trial which simulates an actual implant component. In particular, when dealing with component parts which are to be offset from one another, these assemblies are relatively complex, requiring the selection of appropriate parts and the utilization of a variety of tools, instruments and fixtures for effecting proper assembly, with all parts appropriately affixed and oriented relative to one another. As a result, the trialing procedure can become cumbersome, tedious and time-consuming, to the detriment of the surgeon performing the implant procedure, and ultimately to the detriment of the patient receiving a prosthetic joint implant.

The present invention facilitates the assembly of a trial component having a securement part and an articulation part and, in particular, wherein the parts are offset relative to one another, for quickly and easily verifying the accuracy of the preparation of an implant site. As such, the present invention attains several objects and advantages, some of which are summarized as follows: Enables component parts of a trialing system to be assembled, and selectively disassembled, quickly and easily for a rapid and effective trialing procedure wherein the accuracy of the preparation of an implant site for the reception of a prosthetic joint component is verified; facilitates the assembly and use of a trialing system in which parts of a prosthetic joint component are offset relative to one another; accomplishes quick and accurate assembly, and selective disassembly, of an offset trial without requiring supplemental tools, instruments or fixtures to attain a desirable result; provides increased versatility in accommodating a range of sizes and orientation in an offset trial; allows quick assembly and selective disassembly of parts of an offset trial while preventing inadvertent disassembly; enables increased ease in accomplishing a trialing procedure for joint arthroplasty, with greater accuracy and in less time, to the benefit of the surgeon as well as the patient; provides a trialing system of rugged construction for effective and reliable use over a relatively long service life.

The above objects and advantages, as well as further objects and advantages, are attained by the present invention which may be described briefly as an improvement in a trialing system for use in connection with the implant of a prosthetic joint component having a first part for engaging bone at an implant site to secure the component at the implant site, and a second part for enabling articulation of the prosthetic joint, the improvement facilitating selective connection and disconnection between a trial first member corresponding to the first part of the prosthetic joint component and extending along a first longitudinal axis for extending longitudinally into the bone, and a trial second member corresponding to the second part of the prosthetic joint component, with the second member aligned with a second longitudinal axis offset from the first longitudinal axis, the improvement comprising: an offset adapter; a first coupling arrangement for coupling the offset adapter to the first member, with the first member aligned with the first longitudinal axis; a second coupling arrangement for coupling the second member to the offset adapter, with the second member aligned with the second longitudinal axis offset from the first longitudinal axis, the second coupling arrangement including: a post projecting in a longitudinal direction and a socket essentially complementary to the post and extending in the longitudinal direction for receiving the post within the socket in a seated engagement upon reception of the post within the socket, the longitudinal direction being aligned with the second longitudinal axis; a detent arrangement providing detent elements located along the post and the socket and extending in a transverse direction for engagement upon seating of the post within the socket to retain the second member coupled with the offset adapter; and an access arrangement for accessing the detent arrangement when the post is seated within the socket, the access arrangement enabling access to the detent arrangement for selective actuation of the detent arrangement to release the engagement of the detent elements and permit disengagement of the post and the socket for release of the second member from the offset adapter such that the second member is selectively released in response to actuation of the detent arrangement for selective replacement.

In addition, the present invention provides an improvement in a trialing system for use in connection with the implant of a prosthetic joint component having a first part for engaging bone at an implant site to secure the component at the implant site, and a second part for enabling articulation of the prosthetic joint, the improvement facilitating selective connection and disconnection between a trial first member corresponding to the first part of the prosthetic joint component and extending along a first longitudinal axis for extending longitudinally into the bone, and a trial second member corresponding to the second part of the prosthetic joint component, with the second member aligned with a second longitudinal axis offset from the first longitudinal axis, the improvement comprising: an offset adapter; a first coupling arrangement for coupling the offset adapter to the first member, with the first member aligned with the first longitudinal axis;

a second coupling arrangement for coupling the second member to the offset adapter, with the second member aligned with the second longitudinal axis offset from the first longitudinal axis, the second coupling arrangement including: a post projecting in a longitudinal direction and a socket complementary to the post and extending in the longitudinal direction for receiving the post within the socket in a seated engagement upon reception of the post within the socket, the longitudinal direction being aligned with the second longitudinal axis; and a key and a plurality of notches spaced apart angularly about the second longitudinal axis, each notch being complementary to the key such that engagement of the key with a selected notch will place the post and the socket in one of a plurality of angular orientations relative to one another for engagement of the second member with the offset adapter in a corresponding selected angular orientation relative to the offset adapter.

Further, the present invention includes an improvement in a trialing method for use in connection with the implant of a prosthetic joint component having a first part for engaging bone at an implant site to secure the component at the implant site, and a second part for enabling articulation of the prosthetic joint, the improvement facilitating selective connection and disconnection between a trial first member corresponding to the first part of the prosthetic joint component and extending along a first longitudinal axis for extending longitudinally into the bone, and a trial second member corresponding to the second part of the prosthetic joint component, with the second member aligned with a second longitudinal axis offset from the first longitudinal axis, the improvement comprising: coupling an offset adapter to the first member, with the first member aligned with the first longitudinal axis; coupling the second member to the offset adapter, with the second member aligned with the second longitudinal axis offset from the first longitudinal axis, the coupling of the second member to the offset adapter including: seating a post within a socket along a longitudinal direction aligned with the second longitudinal axis; engaging detent elements located along the post and the socket in response to seating of the post within the socket to retain the second member coupled with the offset adapter; and selectively releasing the engagement of the detent elements to permit selective disengagement of the post and the socket for release of the second member from the offset adapter such that the second member is selectively released in response to release of the detent elements for selective replacement of the second member with an alternate second member.

Still further, the present invention provides an improvement in a trialing method for use in connection with the implant of a prosthetic joint component having a first part for engaging bone at an implant site to secure the component at the implant site, and a second part for enabling articulation of the prosthetic joint, the improvement facilitating selective connection and disconnection between a trial first member corresponding to the first part of the prosthetic joint component and extending along a first longitudinal axis for extending longitudinally into the bone, and a trial second member corresponding to the second part of the prosthetic joint component, with the second member aligned with a second longitudinal axis offset from the first longitudinal axis, the improvement comprising: coupling an offset adapter to the first member, with the first member aligned with the first longitudinal axis; coupling the second member to the offset adapter, with the second member aligned with the second longitudinal axis offset from the first longitudinal axis, the coupling of the second member to the offset adapter including: seating a post within a socket along a longitudinal direction aligned with the second longitudinal axis; and placing the post and the socket in a selected one of a plurality of angular orientations relative to one another for engagement of the second member with the offset adapter in a corresponding selected angular orientation relative to the offset adapter.

Further yet, the present invention includes an improvement in a trialing system for use in connection with the implant of a prosthetic joint component having a first part for engaging bone at an implant site to secure the component at the implant site, and a second part for enabling articulation of the prosthetic joint, the improvement facilitating selective connection and disconnection between a trial first member corresponding to the first part of the prosthetic joint component and extending along a first longitudinal axis for extending longitudinally into the bone, and a trial second member corresponding to the second part of the prosthetic joint component, with the second member aligned with a second longitudinal axis offset from the first longitudinal axis, the improvement comprising: an offset portion integral with the first member such that the offset portion is aligned with the second longitudinal axis and the first member is aligned with the first longitudinal axis; a coupling arrangement for coupling the second member to the offset portion, with the second member aligned with the second longitudinal axis offset from the first longitudinal axis, the coupling arrangement including: a post projecting in a longitudinal direction and a socket essentially complementary to the post and extending in the longitudinal direction for receiving the post within the socket in a seated engagement upon reception of the post within the socket, the longitudinal direction being aligned with the second longitudinal axis; a detent arrangement providing detent elements located along the post and the socket and extending in a transverse direction for engagement upon seating of the post within the socket to retain the second member coupled with the offset portion; and an access arrangement for accessing the detent arrangement when the post is seated within the socket, the access arrangement enabling access to the detent arrangement for selective actuation of the detent arrangement to release the engagement of the detent elements and permit disengagement of the post and the socket for release of the second member from the offset portion such that the second member is selectively released in response to actuation of the detent arrangement for selective replacement.

The present invention will be understood more fully, while still further objects and advantages will become apparent, in the following detailed description of preferred embodiments of the invention illustrated in the accompanying drawing, in which.

Figure 9:
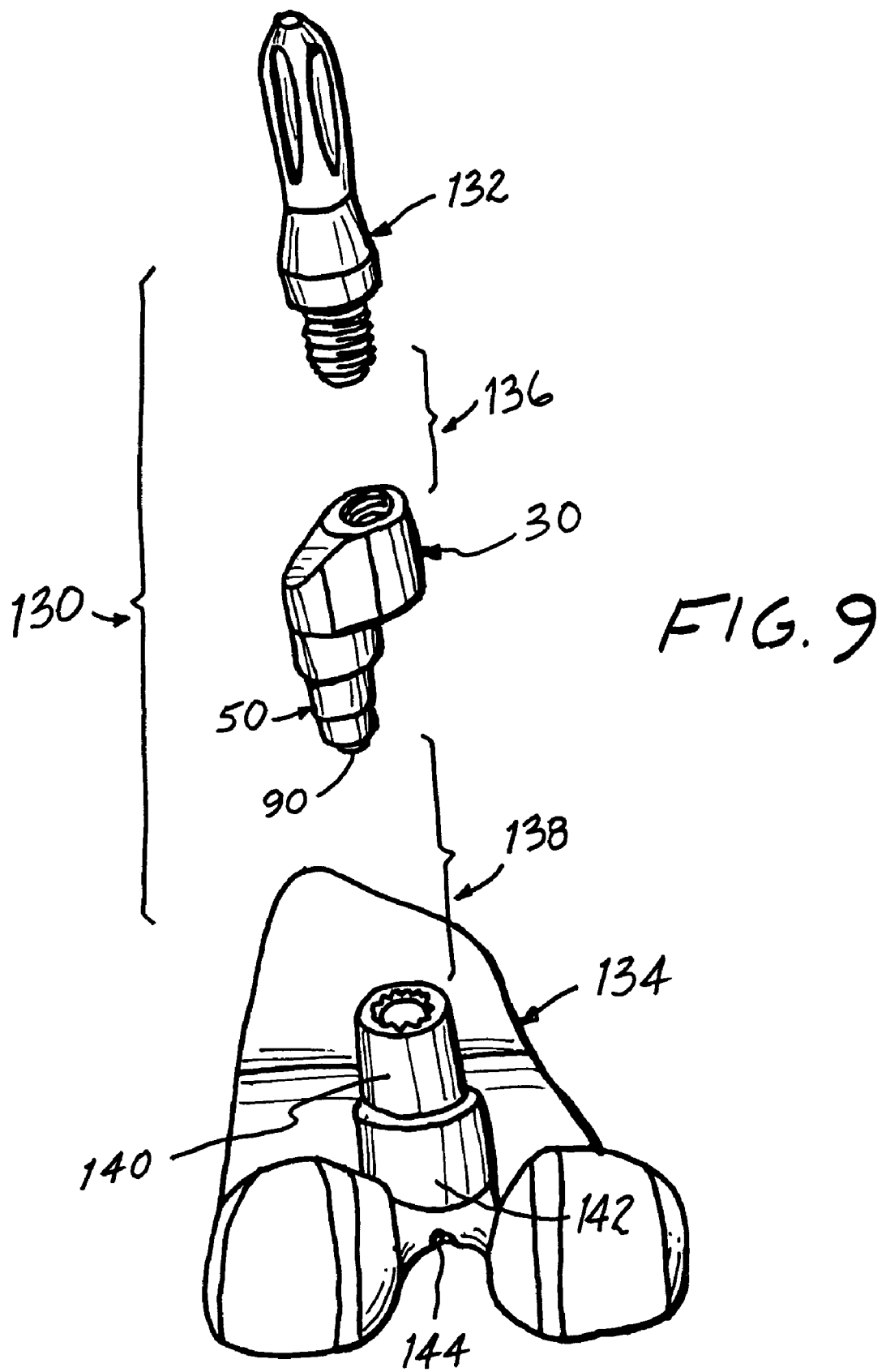
Figure 10:
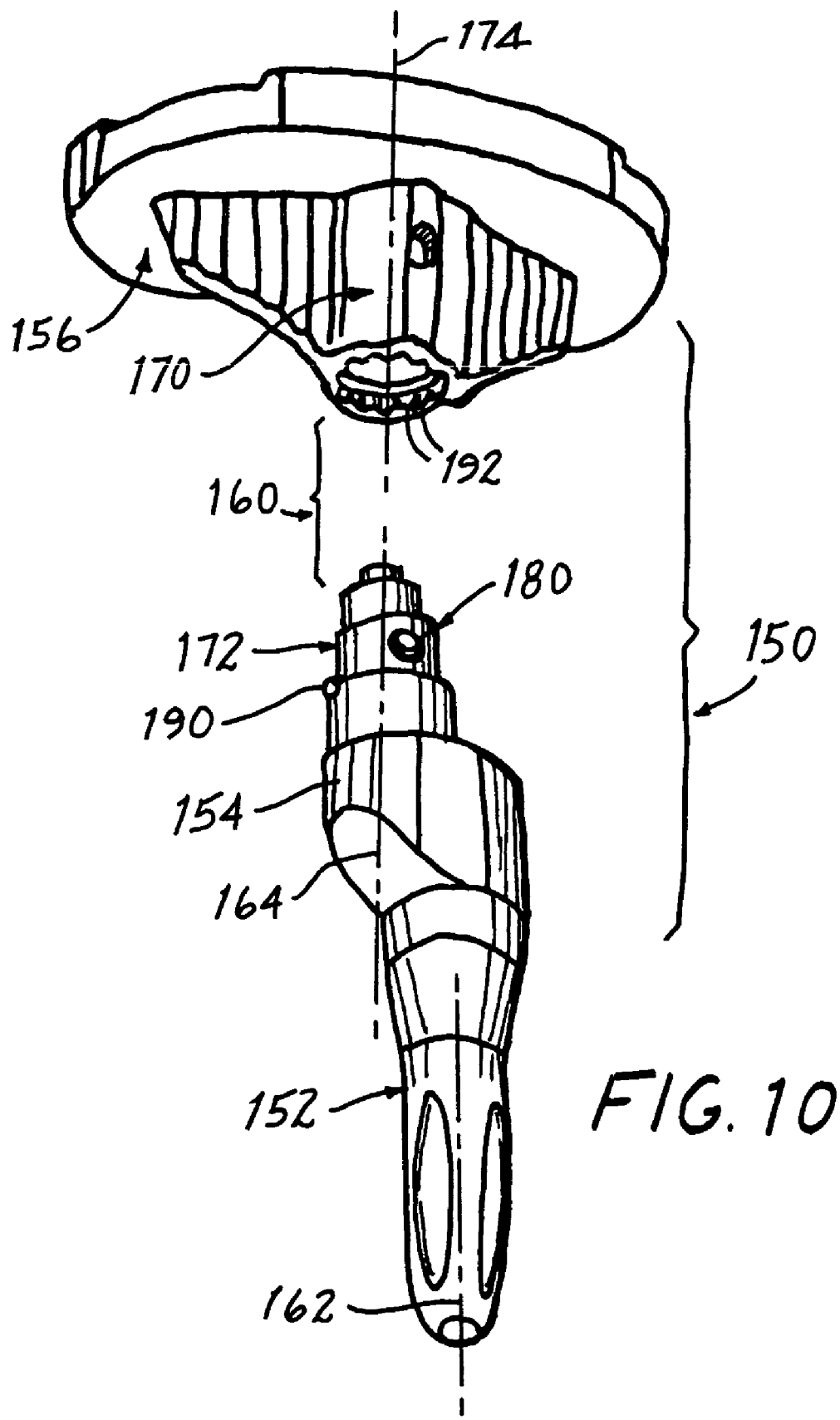

FIG. 9 is an exploded pictorial view illustrating a trial for use in a trialing system having component parts constructed and being used in accordance with another embodiment of the present invention; and FIG. 10 is an exploded pictorial view illustrating a trial for use in a trialing system having component parts constructed and being used in accordance with still another embodiment of the present invention.

Figure 1:
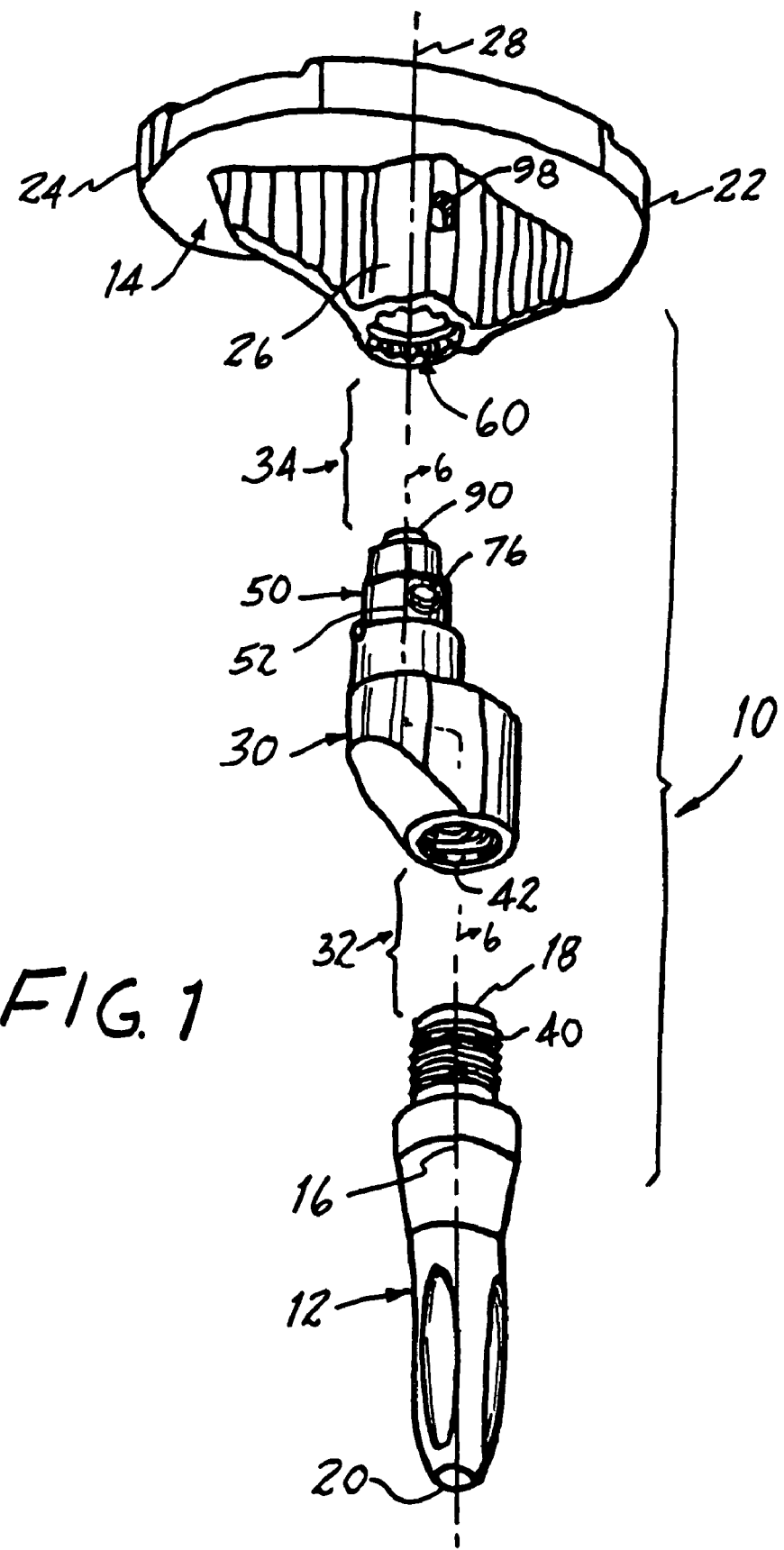
FIG. 1 is an exploded pictorial view illustrating a trial for use in a trialing system having component parts constructed and being used in accordance with the present invention.

Referring now to the drawing, and especially to FIG. 1 thereof, a trial constructed in accordance with the present invention for use in connection with the implant of a prosthetic joint component in the form of a tibial component of a prosthetic knee is illustrated in the form of a tibial trial 10 to be placed at an implant site on a tibia, the implant site having been prepared to receive the actual tibial component, for evaluation of the accuracy of the preparation prior to implanting the actual tibial component. Trial 10 includes a first member in the form of a trial stem 12 which corresponds to the actual stem provided on the actual tibial component for engaging the bone at the implant site to secure the tibial component at the implant site in a now conventional manner. Trial 10 further includes a second member in the form of a trial tibial baseplate 14 corresponding to the actual tibial baseplate provided on the actual tibial component for enabling articulation of the prosthetic knee by means of a bearing member carried by the tibial baseplate, as is now conventional in a prosthetic knee joint. Trial stem 12 extends along a longitudinal axis 16 between a proximal end 18 and a distal end 20. Trial tibial baseplate 14 extends laterally between a lateral edge 22 and a medial edge 24, and includes a sleeve 26 which extends longitudinally along an axis 28 placed intermediate the lateral and medial edges 22 and 24.

For the purpose of trialing, trial stem 12 and trial tibial baseplate 14 are selected in accordance with the size and configuration of the corresponding parts of the actual tibial component to be implanted. The trial stem 12 and the trial tibial baseplate 14 then are assembled to represent the actual tibial component during the trialing procedure. While in many instances such assembly may require merely joining sleeve 26 of the trial tibial baseplate 14 directly to an appropriate trial stem 12, placing axis 28 coextensive with axis 16, as a result of variations in the anatomy of recipients, it may become necessary to assemble the trial tibial baseplate 14 with the trial stem 12 with axis 28 offset from axis 16 by some amount of offset, the amount of offset being dictated by the particular anatomy encountered at the implant site. In a currently conventional manner, the amount of offset required at a particular implant site is determined by instrumentation employed during preparation of the implant site for the reception of the actual tibial component.

Figure 2:
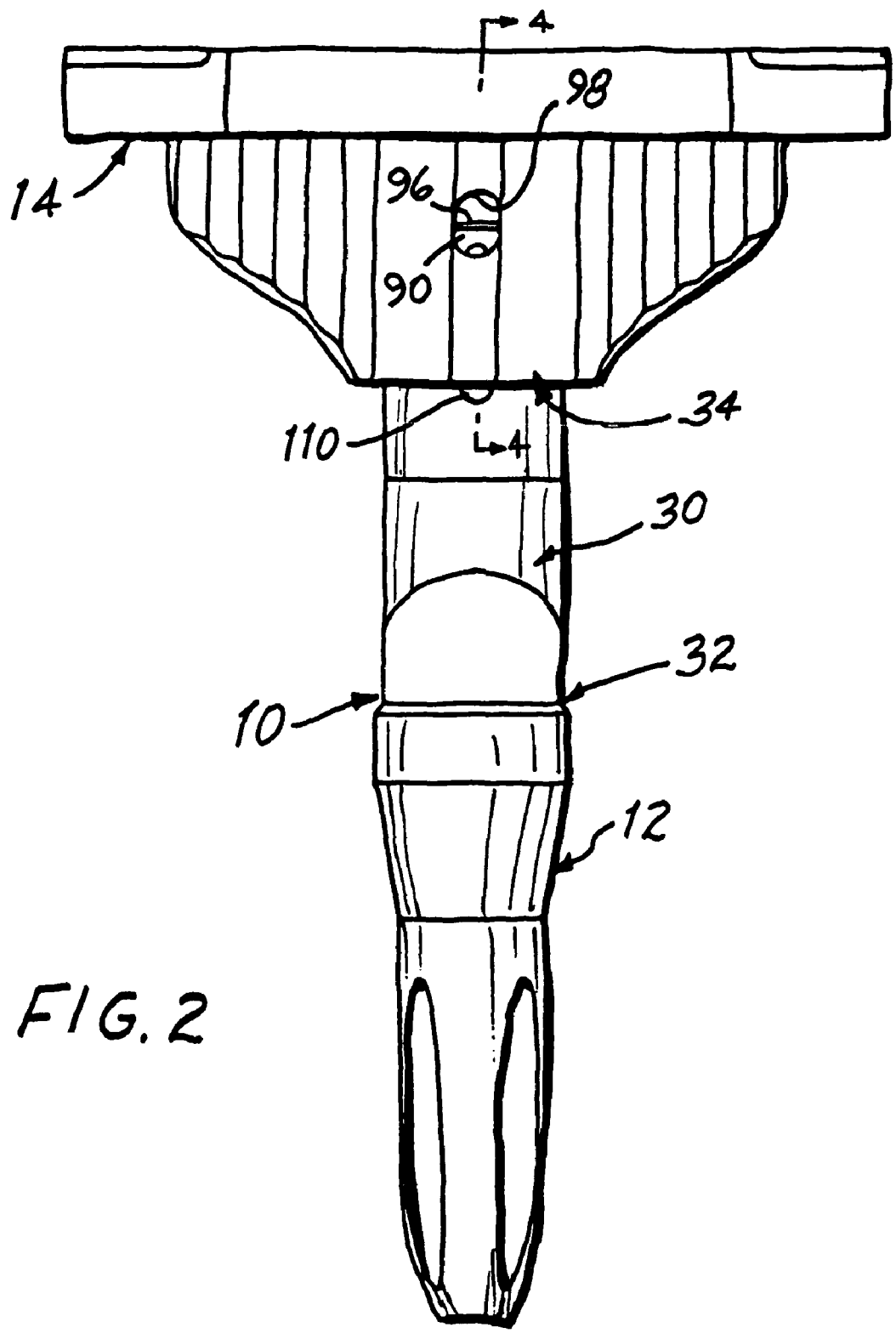
FIG. 2 is a front elevational view showing the component parts assembled.
Figure 3:
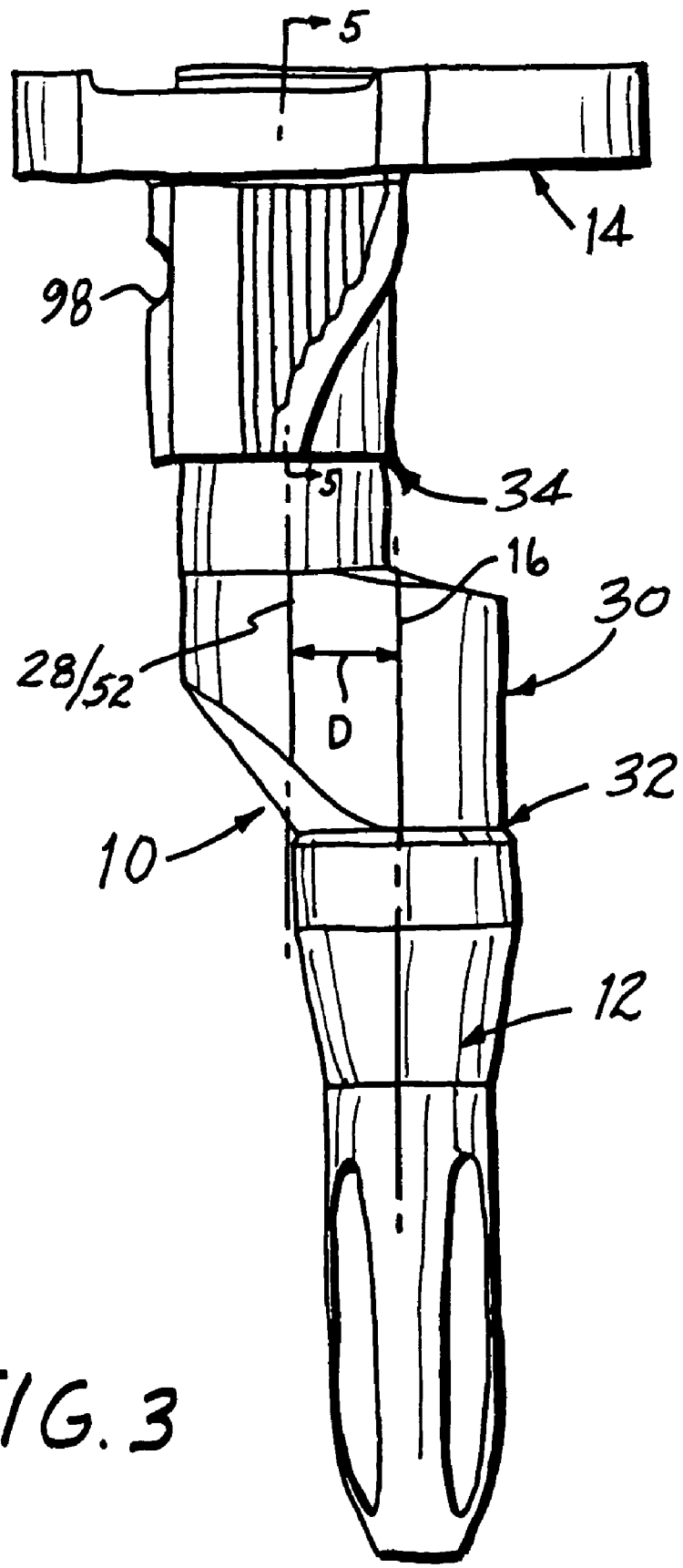
FIG. 3 is a side elevational view showing the component parts assembled.

With the required amount of offset predetermined, an offset adapter 30 is selected based upon the predetermined value of offset required and the selected offset adapter 30 is interposed between the trial stem 12 and the trial tibial baseplate 14. Turning to FIGS. 2 and 3, a first coupling arrangement 32 couples adapter 30 to trial stem 12, and a second coupling arrangement 34 couples trial baseplate 14 to adapter 30 to complete the assembly of trial 10. Returning briefly to FIG. 1, first coupling arrangement 32 includes a threaded stud 40 integral with trial stem 12 at the proximal end 18 of the trial stem 12 and extending along axis 16 to be engaged by a complementary threaded hole 42 in the adapter 30 for securing adapter 30 upon trial stem 12, as illustrated in FIGS. 2 and 3.

Figure 4:
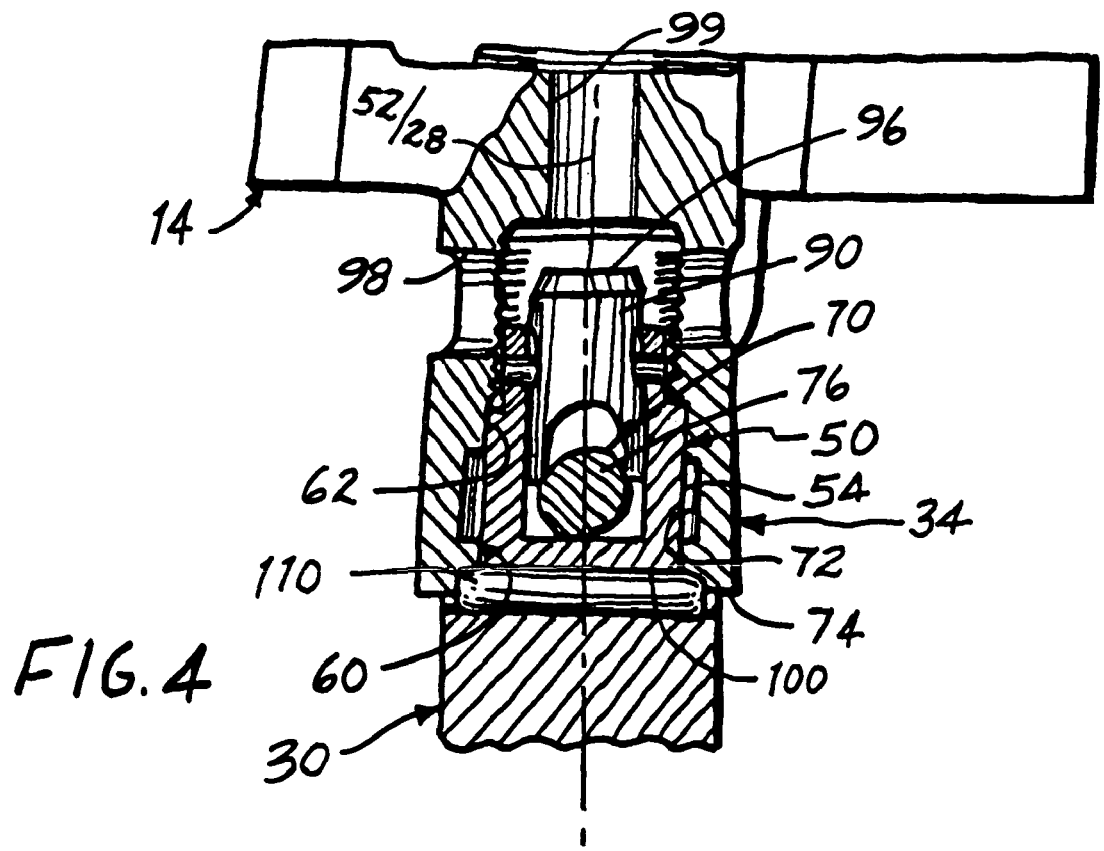
FIG. 4 is an enlarged fragmentary longitudinal cross-sectional view taken along line 4-4 of FIG. 2.
Figure 5:
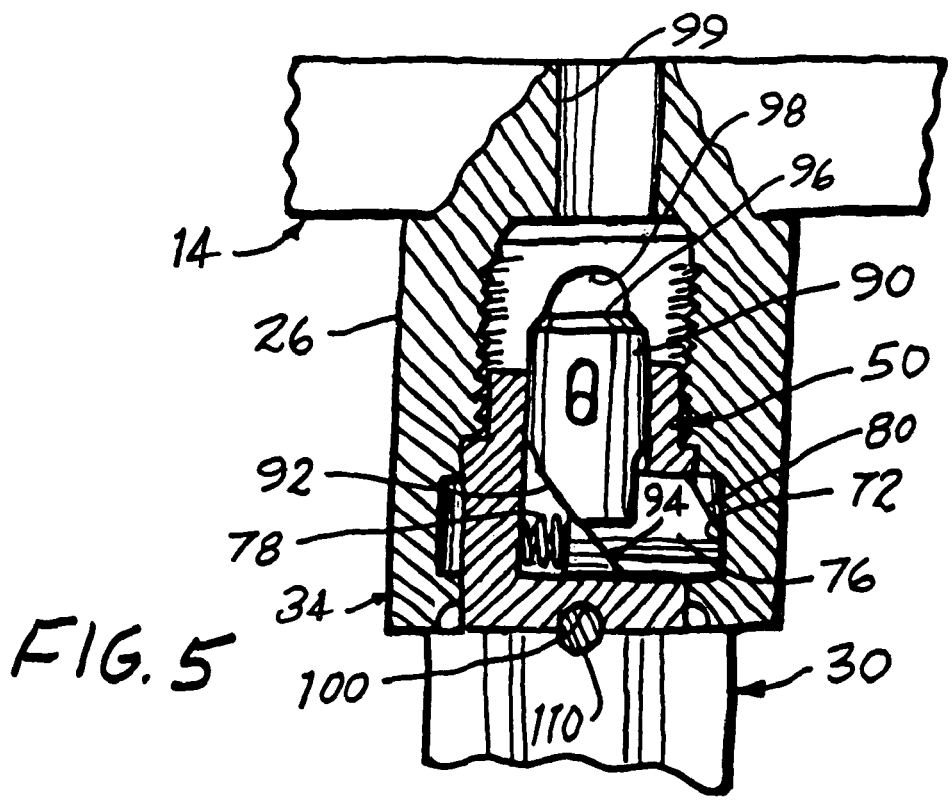
FIG. 5 is an enlarged fragmentary longitudinal cross-sectional view taken along line 5-5 of FIG. 3.

Referring now to FIGS. 4 and 5, as well as to FIGS. 1 through 3, second coupling arrangement 34 includes a post 50 projecting in a longitudinal direction along an axis 52, the preferred configuration of post 50 providing a generally cylindrical outer surface 54 coaxial with axis 52. Sleeve 26 of trial tibial baseplate 14 includes a socket 60 essentially complementary to post 50, having a generally cylindrical inner surface 62 extending coaxial with axis 28 such that post 50 is received readily in seated engagement within socket 60 to couple trial tibial baseplate 14 and adapter 30, placing axis 28 coincident with axis 52. With the trial tibial baseplate 14 thus assembled with the trial stem 12, through the interposed adapter 30, the distance D between axis 16 and axis 28 (see FIG. 3) represents the amount of offset provided by the adapter 30 in the assembled trial 10.

Figure 6:
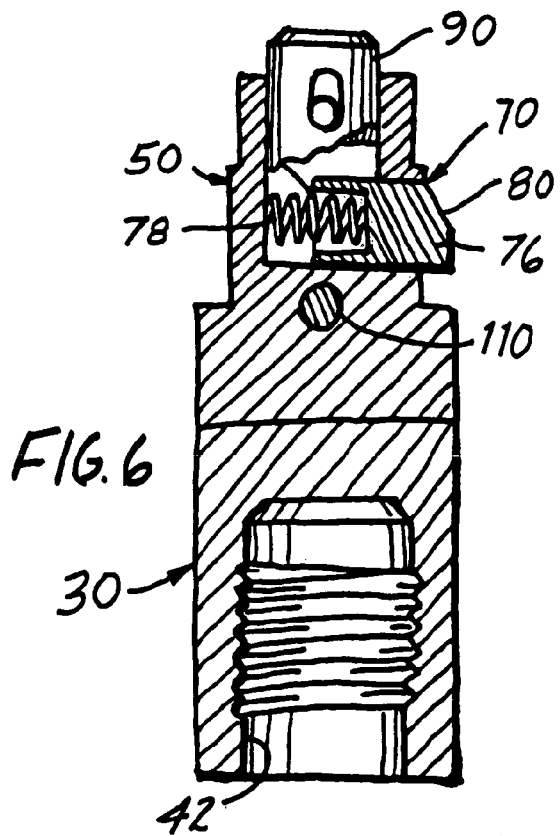
FIG. 6 is an enlarged longitudinal cross-sectional view taken along line 6-6 of FIG. 1.

In order to retain trial tibial baseplate 14 assembled with adapter 30, and consequently with trial stem 12, second coupling arrangement 34 includes a detent arrangement 70 having detent elements extending in a transverse direction and interposed between the post 50 and the socket 60. Referring now to FIG. 6, as well as to FIGS. 4 and 5, the detent elements of detent arrangement 70 include a recess in socket 60, the recess preferably being in the form of an annular groove 72 extending laterally from the inner surface 62 of socket 60 and spaced axially superiorly a relatively short distance from a distal rim 74 of the socket 60, a projection in the form of a detent pin 76 carried by the post 50 for movement in lateral directions relative to the post 50, the projection being juxtaposed with the groove 72 upon seating of the post 50 within the socket 60, and a biasing element in the form of a helical spring 78 biasing the pin 76 toward the groove 72. As the post 50 is inserted into the socket 60, a chamfer 80 will engage the rim 74 of the socket 60 to retract the pin 76 toward the post 50, against the biasing force of helical spring 78, and thereby enable the pin 76 to enter the socket 60. Upon registration of the pin 76 in juxtaposition with the groove 72, the pin 76 will snap into the groove 72, in response to the biasing force of helical spring 78, and the trial tibial baseplate 14 will be coupled to the adapter 30.

When it is desired to disassemble the trial tibial baseplate 14 from the adapter 30, an access arrangement enables access to the detent arrangement 70 for selective disengagement of the pin 76 from the groove 72 by the operation of an actuator, shown in the form of a plunger 90 coupled with the pin 76 for movement of the pin 76 in a lateral direction against the biasing force of helical spring 78 to retract the pin 76 from the groove 72. To that end, plunger 90 is mounted for sliding movement in longitudinal directions within the post 50 and carries a cam surface 92 engaged with a follower surface 94 on the pin 76. An operating end 96 of the plunger 90 is spaced from the post 50 in a superior direction and is accessible through an opening 98 in the sleeve 26 of the trial tibial baseplate 14. Thus, by engaging the operating end 96 of the plunger 90 and depressing the plunger 90, in an inferior direction, pin 76 is retracted from groove 72 and the trial tibial baseplate 14 is selectively released readily from the adapter 30. Alternately, access to plunger 90 is available through another opening 99 extending through baseplate 14 along axis 28 for depression of plunger 90 to effect retraction of pin 76.

The ready release of trial tibial baseplate 14 enables rapid and easy replacement of the trial tibial baseplate 14 with alternate trial tibial baseplates, and the ready employment of alternate offset adapters, as well as facilitating the selection of alternate angular orientations of the baseplate 14 relative to the offset adapter 30, as will be described below, during a trialing procedure, without the necessity for special or complex tools and instruments and without requiring cumbersome and complex assembly and disassembly operations. The quick-connect and quick-disconnect provided by the detent arrangement 70 of adapter 30 facilitates the trialing procedure, resulting in greater accuracy achieved in less time, thus assisting the surgeon and ultimately benefitting the recipient of the prosthetic knee.

Figure 7:
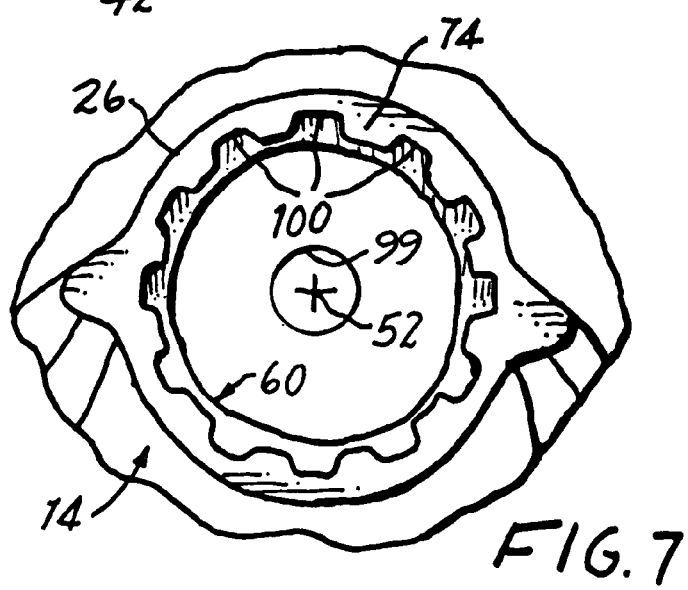
FIG. 7 is an enlarged fragmentary bottom plan view of a component part in the form of a tibial baseplate of the trial.

Turning now to FIG. 7, as well as to FIGS. 1 through 6, adapter 30 enables the coupling of trial tibial baseplate 14 and the adapter 30 with the trial tibial baseplate 14 oriented at any selected one of a plurality of angular positions about axis 52, relative to adapter 30. To that end, the second coupling arrangement 34 includes a plurality of notches 100 extending transversely across and axially into the sleeve 26 at distal rim 74 of the socket 60, the notches 100 being spaced apart angularly about axis 52 so as to be placed at a plurality of circumferentially spaced apart angular locations. A key in the form of an orienting pin 110 extends in longitudinal and transverse directions along the post 50 and is complementary to notches 100 such that upon alignment of pin 110 with a selected notch 100, trial tibial baseplate 14 will be seated upon post 50 at a corresponding selected angular orientation relative to the adapter 30. It is noted that the annular configuration of groove 72 enables detent pin 76 to engage groove 72 when the trial tibial baseplate 14 is seated upon adapter 30 in any selected one of the available plurality of angular orientations. In this manner, a single selected trial tibial baseplate 14 is coupled to adapter 30 at any selected one of a plurality of available angular orientations relative to the adapter 30 with ease and accuracy.

Figure 8:
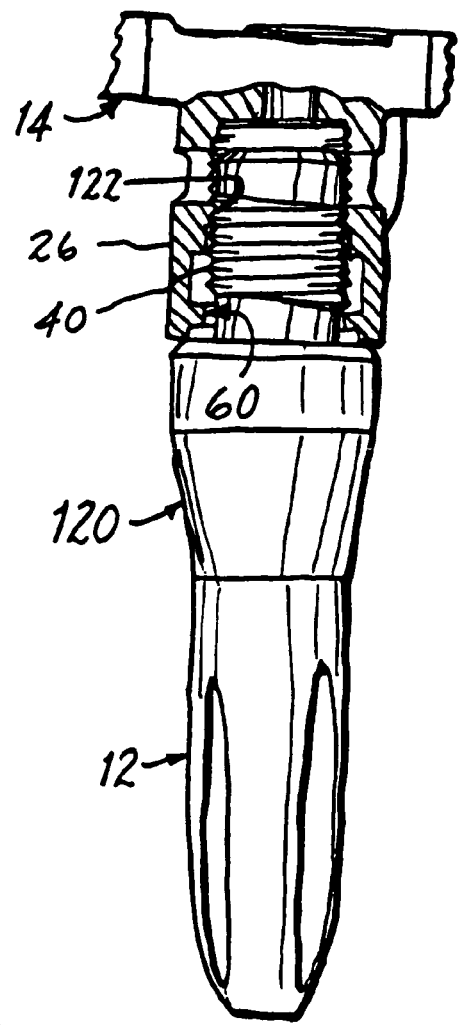
FIG. 8 is a front elevational view, partially sectioned, illustrating an alternate arrangement.

Referring now to FIG. 8, there is illustrated an alternate tibial trial 120 in which there is no offset between the trial tibial baseplate 14 and the trial stem 12. Should there be a requirement for such a tibial trial having no offset between the trial tibial baseplate and the stem, adapter 30 merely is deleted and trial stem 12 is coupled directly to trial tibial baseplate 14. In order to effect such a coupling, sleeve 26 of trial tibial baseplate 14 includes an internal thread 122 complementary to threaded stud 40 of trial stem 12 and extending axially within sleeve 26 from socket 60 in a superior direction. Assembly of tibial trial 120 is accomplished merely by threading stud 40 into thread 122, with no requirement for additional component parts in order to enable the construction of the alternative configuration of tibial trial 120. Alternately, threaded stud 40 of trial stem 12 may be replaced with a post constructed in the manner of post 50 with detent elements similar to those of detent arrangement 70 for coupling baseplate 14 directly to trial stem 12 in the manner described above in connection with coupling the baseplate 14 with adapter 30.

In the embodiment illustrated in FIG. 9, a trial constructed in accordance with the present invention is shown for use in connection with the implant of a prosthetic joint component in the form of a femoral component of a prosthetic knee and is in the form of a femoral trial 130 to be placed at an implant site on a femur. Accordingly, rather than having a trial tibial baseplate assembled with a trial stem, a trial stem 132 of femoral trial 130 is to be assembled with a trial condylar member 134. When there is a requirement for an offset between the trial stem 132 and the trial condylar member 134 in the assembled femoral trial 130, a selected offset adapter 30 is interposed between the trial stem 132 and the trial condylar member 134.

A first coupling arrangement 136 is provided for coupling the trial stem 132 to the adapter 30. First coupling arrangement 136 is constructed as described above in connection with first coupling arrangement 32 of the above-described tibial trial 10 and is operated in the same manner as first coupling arrangement 32 to assemble trial stem 132 with adapter 30.

A second coupling arrangement 138 is provided for coupling the trial condylar member 134 to adapter 30. Second coupling arrangement 138 is constructed as described above in connection with second coupling arrangement 34 of the tibial trial 10, the second coupling arrangement 138 including a sleeve 140 having essentially the same construction as sleeve 26 and being placed at an intercondylar location 142 for the reception of post 50 of adapter 30. Operation of the second coupling arrangement 138 is accomplished in the same manner as second coupling arrangement 34 to assemble trial condylar member 134 with adapter 30. Selective disassembly of the condylar member 134 from adapter 30 is enabled by virtue of access to plunger 90 of adapter 30 through an opening 144 at the intercondylar location 142.

Selective assembly and disassembly of the femoral trial 130 is accomplished with ease and with accuracy, adapter 30 serving to simplify and expedite the affixation of a selected trial condylar member 134 in the femoral trial 130, and selective removal of the trial condylar member 134 for substitution with alternate trial condylar members, and the ready employment of alternate offset adapters, as well as facilitating the selection of alternate angular orientations of the trial condylar member 134 relative to the adapter 30, in the manner described above in connection with the tibial trial 10, as may be required during a trialing procedure.

In the embodiment of FIG. 10, a tibial trial 150 includes a trial stem 152 provided with an integrated offset portion 154, and a trial tibial baseplate 156 is assembled with the trial stem 152 by means of a coupling arrangement 160. Trial stem 152 extends along an axis 162 and offset portion 154 provides an axis 164 offset from axis 162 by a prescribed offset distance. In the illustrated embodiment, offset portion 154 is unitary with trial stem 152; however, it is to be understood that offset portion 154 may be constructed separately and then joined with trial stem 152 to establish an integral structure.

Coupling arrangement 160 is constructed as described above in connection with second coupling arrangement 34 of tibial trial 10, the coupling arrangement 160 including a sleeve 170 having essentially the same construction as sleeve 26 for the reception of a post 172, constructed similar to post 50, the sleeve 170 extending along an axis 174 and the post 172 extending along axis 164. A detent arrangement 180 is constructed and operated in the same manner as detent arrangement 70 for selective assembly and disassembly of trial stem 152 and trial tibial baseplate 156. Thus, trial tibial baseplate 156 is assembled with trial stem 152 with axis 174 aligned with axis 164, providing the desired offset from axis 162. As described above, upon such assembly a key 190 on the post 172 is engaged with one of several alternate notches 192 in sleeve 170 to secure the assembled trial tibial baseplate 156 and trial stem 152 in a selected angular orientation of the trial tibial baseplate 156 relative to the trial stem 152.

It will be seen that the present invention attains the objects and advantages summarized above, namely: Enables component parts of a trialing system to be assembled, and selectively disassembled, quickly and easily for a rapid and effective trialing procedure wherein the accuracy of the preparation of an implant site for the reception of a prosthetic joint component is verified; facilitates the assembly and use of a trialing system in which parts of a prosthetic joint component are offset relative to one another; accomplishes quick and accurate assembly, and selective disassembly, of an offset trial without requiring supplemental tools, instruments or fixtures to attain a desirable result; provides increased versatility in accommodating a range of sizes and orientation in an offset trial; allows quick assembly and selective disassembly of parts of an offset trial while preventing inadvertent disassembly; enables increased ease in accomplishing a trialing procedure for joint arthroplasty, with greater accuracy and in less time, to the benefit of the surgeon as well as the patient; provides a trialing system of rugged construction for effective and reliable use over a relatively long service life.

It is to be understood that the above detailed description of preferred embodiments of the invention are provided by way of example only. Various details of design, construction and procedure may be modified without departing from the true spirit and scope of the invention as set forth in the appended claims.

The embodiments of the invention in which an exclusive property or privilege is claimed are defined as follows:

1. An improvement in a trialing system for use in connection with the implant of a prosthetic joint component having a first part for engaging bone at an implant site to secure the component at the implant site, and a second part for enabling articulation of the prosthetic joint, the improvement facilitating selective connection and disconnection between a trial first member corresponding to the first part of the prosthetic joint component and extending along a first longitudinal axis for extending longitudinally into the bone, and a trial second member corresponding to the second part of the prosthetic joint component, with the second member aligned with a second longitudinal axis offset from the first longitudinal axis, the improvement comprising:

an offset adapter;
a first coupling arrangement for coupling the offset adapter to the first member, with the first member aligned with the first longitudinal axis;
a second coupling arrangement for coupling the second member to the offset adapter, with the second member aligned with the second longitudinal axis offset from the first longitudinal axis, the second coupling arrangement including:
a post projecting in a longitudinal direction and a socket essentially complementary to the post and extending in the longitudinal direction for receiving the post within the socket in a seated engagement upon reception of the post within the socket, the longitudinal direction being aligned with the second longitudinal axis;
a detent arrangement providing detent elements located along the post and the socket and extending in a transverse direction for engagement upon seating of the post within the socket to retain the second member coupled with the offset adapter; and
an access arrangement located within the second coupling arrangement in position to provide access to the detent arrangement when the post is seated within the socket, the access arrangement including a first opening extending in the transverse direction through the second member and communicating with the detent arrangement, and a second opening extending in the longitudinal direction through the second member and communicating with the detent arrangement to enable selective access to the detent arrangement through either one of the first opening and the second opening for selective actuation of the detent arrangement to release the engagement of the detent elements and permit disengagement of the post and the socket for release of the second member from the offset adapter such that the second member is selectively released in response to actuation of the detent arrangement for selective replacement.

2. The improvement of claim 1 wherein:
the detent arrangement includes a lateral recess, a laterally extending projection, and a biasing element for resiliently biasing the projection laterally into engagement with the recess with a biasing force.

3. The improvement of claim 2 including an actuator coupled with the projection for selectively moving the projection laterally against the biasing force to disengage the projection from the recess.

4. The improvement of claim 3 wherein the actuator includes a plunger extending in a longitudinal direction and movable longitudinally, the plunger being coupled with the projection to move the projection laterally out of the recess in response to longitudinal movement of the plunger.

5. The improvement of claim 4 wherein the post extends longitudinally along the adapter and the socket extends longitudinally into the second member.

6. The improvement of claim 5 wherein the recess extends laterally into the second member, the projection is mounted in the post for lateral movement into and out of the recess, and the plunger extends into the post in a longitudinal direction and is movable longitudinally to move the projection laterally, against the biasing force, out of the recess.

7. The improvement of claim 6 wherein the recess has an annular configuration enabling lateral movement of the projection into and out of the recess in any one of a plurality of angular positions of the post and the socket relative to one another about the second longitudinal axis.

8. The improvement of claim 3 wherein the post is receivable within the socket with the post seated within the socket in any one of a plurality of angular positions relative to one another about the second longitudinal axis, the second coupling arrangement includes a key and a plurality of notches spaced apart angularly about the second longitudinal axis, each notch being complementary to the key such that engagement of the key with a selected notch will place the post and the socket in one of the plurality of angular orientations relative to one another for securement of the second member in a corresponding selected angular orientation relative to the offset adapter.

9. The improvement of claim 8 wherein the key extends in longitudinal and transverse directions along the post, and the notches are spaced circumferentially around the socket for engagement of the key with a selected notch.

10. The improvement of claim 9 wherein the recess has an annular configuration enabling lateral movement of the projection into and out of the recess in any one of a plurality of angular positions of the post and the socket relative to one another about the second longitudinal axis.

11. An improvement in a trialing method for use in connection with the implant of a prosthetic joint component having a first part for engaging bone at an implant site to secure the component at the implant site, and a second part for enabling articulation of the prosthetic joint, the improvement facilitating selective connection and disconnection between a trial first member corresponding to the first part of the prosthetic joint component and extending along a first longitudinal axis for extending longitudinally into the bone, and a trial second member corresponding to the second part of the prosthetic joint component, with the second member aligned with a second longitudinal axis offset from the first longitudinal axis, the improvement comprising:

coupling an offset adapter to the first member, with the first member aligned with the first longitudinal axis;
coupling the second member to the offset adapter, with the second member aligned with the second longitudinal axis offset from the first longitudinal axis, the coupling of the second member to the offset adapter including:
seating a post within a socket along a longitudinal direction aligned with the second longitudinal axis;
engaging detent elements located along the post and the socket in response to seating of the post within the socket to retain the second member coupled with the offset adapter; and
accessing the detent elements through either one of an opening extending through the second member in the longitudinal direction and another opening extending through the second member in a direction transverse to the longitudinal direction for selectively releasing the engagement of the detent elements to permit selective disengagement of the post and the socket for release of the second member from the offset adapter such that the second member is selectively released in response to release of the detent elements for selective replacement of the second member with an alternate second member.

12. The improvement of claim 11 including inserting the post within the socket with the post seated within the socket in any selected one of a plurality of angular positions relative to one another about the second longitudinal axis, and securing the second member in a corresponding selected angular orientation relative to the offset adapter.

13. An improvement in a trialing system for use in connection with the implant of a prosthetic joint component having a first part for engaging bone at an implant site to secure the component at the implant site, and a second part for enabling articulation of the prosthetic joint, the improvement facilitating selective connection and disconnection between a trial first member corresponding to the first part of the prosthetic joint component and extending along a first longitudinal axis for extending longitudinally into the bone, and a trial second member corresponding to the second part of the prosthetic joint component, with the second member aligned with a second longitudinal axis offset from the first longitudinal axis, the improvement comprising:
an offset portion integral with the first member such that the offset portion is aligned with the second longitudinal axis and the first member is aligned with the first longitudinal axis;
a coupling arrangement for coupling the second member to the offset portion, with the second member aligned with the second longitudinal axis offset from the first longitudinal axis, the coupling arrangement including:
a post projecting in a longitudinal direction and a socket essentially complementary to the post and extending in the longitudinal direction for receiving the post within the socket in a seated engagement upon reception of the post within the socket, the longitudinal direction being aligned with the second longitudinal axis;
a detent arrangement providing detent elements located along the post and the socket and extending in a transverse direction for engagement upon seating of the post within the socket to retain the second member coupled with the offset portion; and
an access arrangement located within the second member in position to provide access to the detent arrangement when the post is seated within the socket, the access arrangement including a first opening extending in the transverse direction through the second member and communicating with the detent arrangement, and a second opening extending in the longitudinal direction through the second member and communicating with the detent arrangement to enable selective access to the detent arrangement through either one of the first opening and the second opening for selective actuation of the detent arrangement to release the engagement of the detent elements and permit disengagement of the post and the socket for release of the second member from the offset portion such that the second member is selectively released in response to actuation of the detent arrangement for selective replacement.

14. The improvement of claim 13 wherein:
the detent arrangement includes a lateral recess, a laterally extending projection, and a biasing element for resiliently biasing the projection laterally into engagement with the recess with a biasing force.

15. The improvement of claim 14 including an actuator coupled with the projection for selectively moving the projection laterally against the biasing force to disengage the projection from the recess.

16. The improvement of claim 15 wherein the actuator includes a plunger extending in a longitudinal direction and movable longitudinally, the plunger being coupled with the projection to move the projection laterally out of the recess in response to longitudinal movement of the plunger.

17. The improvement of claim 15 wherein the post is receivable withing the socket with the post seated within the socket in any one of a plurality of angular positions relative to one another about the second longitudinal axis, the coupling arrangement includes a key and a plurality of notches spaced apart angularly about the second longitudinal axis, each notch being complementary to the key such that engagement of the key with a selected notch will place the post and the socket in one of the plurality of angular orientations relative to one another for securement of the second member in a corresponding selected angular orientation relative to the offset portion.

18. The improvement of claim 17 wherein the key extends in longitudinal and transverse directions along the post, and the notches are spaced circumferentially around the socket for engagement of the key with a selected notch.

19. The improvement of claim 18 wherein the recess has an annular configuration enabling lateral movement of the projection into and out of the recess in any one of a plurality of angular positions of the post and the socket relative to one another about the second longitudinal axis.

\* \* \* \* \*